US007553910B2

(12) United States Patent
Buding et al.

(10) Patent No.: US 7,553,910 B2
(45) Date of Patent: Jun. 30, 2009

(54) PREPARATION OF DERIVATIZED DITHIOLS

(75) Inventors: Hartmuth Buding, Titz (DE); Hermann-Josef Weidenhaupt, Pulheim (DE); Winfried Jeske, Burscheid (DE); Thomas Kleiner, Odenthal (DE)

(73) Assignee: LANXESS Deutschland GmbH, Leverkusen (DE)

( * ) Notice: Subject to any disclaimer, the term of this patent is extended or adjusted under 35 U.S.C. 154(b) by 473 days.

(21) Appl. No.: 11/136,013

(22) Filed: May 24, 2005

(65) Prior Publication Data
US 2005/0272933 A1 Dec. 8, 2005

(30) Foreign Application Priority Data
May 26, 2004 (DE) .................. 10 2004 025 730

(51) Int. Cl.
*C08C 19/20* (2006.01)
*C08C 19/22* (2006.01)
(52) U.S. Cl. ............... 525/329.3; 525/331.8; 525/332.6
(58) Field of Classification Search ............. 525/329.3, 525/331.8, 332.6
See application file for complete search history.

(56) References Cited
U.S. PATENT DOCUMENTS

| 3,869,436 | A |   | 3/1975 | Trivette, Jr. ............ 260/79.5 C |
| 3,900,471 | A | * | 8/1975 | Dunbar et al. ................ 544/85 |
| 3,979,369 | A |   | 9/1976 | Trivette, Jr. ............ 260/79.5 C |
| 4,417,012 | A |   | 11/1983 | Moniotte ...................... 524/83 |
| 4,520,154 | A |   | 5/1985 | Moniotte ..................... 524/157 |
| 4,587,296 | A |   | 5/1986 | Moniotte ...................... 525/61 |
| 5,342,900 | A | * | 8/1994 | Wolpers et al. .......... 525/329.3 |
| 5,717,038 | A |   | 2/1998 | Horpel et al. ............ 525/332.4 |

FOREIGN PATENT DOCUMENTS

| DE | 10 2004 018 193 | 11/2005 |
| EP | 385 972 | 6/1992 |

OTHER PUBLICATIONS

Houben-Weyl, Methoden der organischen Chemie (Methods of Organic Chemistry), vol. 9, pp. 823-827, Georg Thieme Verlag, Stuttgart, (1955).
Ullmanns Encyklopadie der technischen Chemie, 4th newly revised and extended edition, vol. 21, pp. 89-90, Verlag Chemie, Weinheim (1982).
Ullmanns Encyklopadie der technischen Chemie, 4th newly revised and extended edition, vol. 11, p. 695-696, Verlag Chemie, Weinheim (1976).

* cited by examiner

*Primary Examiner*—Golam M. M. Shameem
*Assistant Examiner*—Susannah Chung
(74) *Attorney, Agent, or Firm*—Nicanor A. Kohncke

(57) ABSTRACT

The invention relates to a process for preparing dithiols derivatized with dithiocarbamic acids, in which the derivatized dithiols are obtained in high yield and purity.

5 Claims, No Drawings

PREPARATION OF DERIVATIZED DITHIOLS

FIELD OF THE INVENTION

The invention relates to a process for preparing dithiols derivatized with dithiocarbamic acids.

BACKGROUND OF THE INVENTION

The preparation of dithiols derivatized with dithiocarbamic acids is known in principle (cf., for example, DE-A 22 56 511 and EP-A 530 590).

DE-A 22 56 511 discloses, inter alia, the synthesis of dithiols derivatized with dithiocarbamic acids via Bunte salts. On page 39, 3rd paragraph, such a synthesis is described using the example of the compound 1,4-bis(hexahydro-1H-azepin-1-ylthiocarbonyl-dithio)-2-butene as follows: 0.1 mol of 1,4-dichlorobutene-2 is reacted at boiling temperature with sodium thiosulphate pentahydrate in aqueous ethanol and the ethanol is subsequently removed by distillation. Further water, 0.3 mol of sodium acetate trihydrate and approx. 0.23 mol of formaldehyde are then added to the aqueous Bunte salt solution. An aqueous solution of sodium hexahydro-1H-azepin-1-ylthiocarbothiolate is then added dropwise at room temperature to this mixture over 0.5 h and the mixture is stirred at room temperature for a further 1.5 h. An organic solvent is not present in the reaction. The oily reaction product is extracted with chloroform at the end of the reaction, and the organic phase is washed with water and dried over anhydrous sodium sulphate. To obtain the 1,4-bis(hexahydro-1H-azepin-1-ylthiocarbonyldithio)-2-butene, the chloroform is evaporated. One disadvantage of this process is the high wastewater pollution by sodium acetate, i.e. owing to the high concentration of sodium acetate, the wastewater has a high chemical oxygen demand (COD). Thus, in the aforementioned example, at the reported yield of 71%, approx. 4.2 mol of sodium acetate are used for 1 mol of prepared product, which constitutes a very unfavourable ratio from an ecological point of view. In the reworking of the general information of DE-A 22 56 511 starting from 1,6-dichlorohexane in relation to the inventive compounds of the formula (I), which are illustrated in detail below, products which were difficult to filter and difficult to wash were additionally obtained in insufficient yield and sometimes insufficient purity (active substance content) (cf. Examples 17 and 18).

With regard to the preparation of dithiols derivatized with dithiocarbamic acids, EP-A 530 590 makes reference, for example, to EP-A 432 417. EP-A 432 417 discloses, as a synthetic route for the preparation of dithiols derivatized with dibenzyldithiocarbamic acid, in a very general manner, the reaction of 1,2-dichloroethane with sodium thiosulphate in aqueous solution and subsequent reaction of the resulting bis-Bunte salt with sodium dibenzyldithiocarbamate (page 4, lines 50 to 56). No remarks are made on reaction parameters to be employed advantageously. Nor are any working examples for the synthesis cited. In-house experiments on the reworking of the general synthesis information of EP-A 432 417 using the example of 1,6-dichlorohexane with regard to the inventive compounds of the formula (I), which are illustrated in detail below, have given rise to products which are difficult to filter and difficult to wash in insufficient yield and sometimes also insufficient purity (active substance content) (cf. Examples 19 and 20).

There is no description of any industrially simple, environmentally friendly and readily practicable preparation process which affords the inventive compounds of the formula (I) in high yields and in high purities.

SUMMARY OF THE INVENTION

It is an object of the present invention to provide a technically simple, economically viable and as far as possible environmentally friendly and readily practicable preparation process for the compounds of the formula (I), which affords products in high yield and purity.

With the prior art preparation processes, the aim set cannot be achieved.

The invention therefore provides a process for preparing compounds of the formula (I)

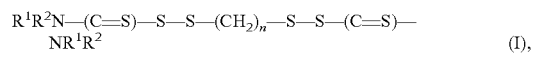
$$R^1R^2N-(C=S)-S-S-(CH_2)_n-S-S-(C=S)-NR^1R^2 \quad (I),$$

in which the $R^1$ and $R^2$ radicals are each independently hydrogen, alkyl, cycloalkyl, aralkyl, phenyl or substituted phenyl or alkylaryl, or, together with the particular nitrogen atom, form a heterocyclic ring having 4 to 8 carbon atoms and n is an integer from 2 to 8, characterized in that the compounds of the formula (II)

$$[R^1R^2N-(C=S)-S]_zMe^1 \quad (II)$$

in which the $R^1$ and $R^2$ radicals are each as defined in the formula (I) and z=1 when $Me^1$ is an alkali metal or ammonium ion and z=2 when $Me^1$ is an alkaline earth metal ion are reacted with the compounds of the formula (III)

$$Me^2O_3SS-(CH_2)_n-SSO_3Me^3 \quad (III)$$

where $Me^2$ and $Me^3$ are the same or different and are each monovalent metal ions or ammonium ions and n is as defined in the formula (I)

in the presence of water, carbonyl compounds and organic solvents in a pH range of 7 to 14 at a reaction temperature of 0° to 90° C. up to a yield of at least 80% of theory based on the compounds of the formula (III), the compounds of the formula (II) being used in amounts of 180 to 250 mol %, based on the moles of compounds of the formula (II) used, the carbonyl compounds in amounts of 5 to 600 mol %, based on the moles of compounds of the formula (III) used, and the organic solvents in amounts of 2 to 100 000 parts by weight based on 100 parts by weight of the theoretically expected amount of compounds of the formula (I).

DETAILED DESCRIPTION OF THE INVENTION

The $R^1$ and $R^2$ radicals in the formulae (I) and (II) are preferably hydrogen, alkyl, straight-chain or branched having 3 to 24 carbon atoms, cycloalkyl having 3 to 8 carbon atoms, aralkyl having 7 to 26 carbon atoms, phenyl, optionally substituted by halogenatoms, nitro and/or OH groups, or alkylaryl having 7 to 26 carbon atoms, or, together with the particular nitrogen atom, form a heterocyclic ring having 4 to 8 carbon atoms.

Examples of alkyl radicals are methyl, ethyl, propyl, i-propyl, n-butyl, i-butyl, sec-butyl, tert-butyl, n-amyl, hexyl, n-octyl, 2-ethylhexyl, decyl, dodecyl, tetradecyl, hexadecyl, octadecyl, eicosyl or docosyl. Examples of cycloalkyl radicals are cyclopropyl, cyclopentyl, methylcyclopentyl, cyclohexyl, methylcyclohexyl, cycloheptyl or cyclooctyl. Examples of aralkyl radicals are benzyl or phenylethyl. Examples of alkylaryl radicals are toluene or xylene.

Examples of the amino radicals $R^1R^2N$ in the formulae (I) and (II) may be derived formally from the amines dimethylamine, diethylamine, dipropylamine, di-i-propylamine, din-butylamine, di-i-butylamine, di-tert-butylamine, dioctylamine, di-2-ethylhexylamine, dinonylamine, dicyclohexylamine, diphenylamine, dibenzylamine, methylphenylamine, ethylphenylamine, phenylcyclohexylamine, phenylbenzylamine or benzylcyclohexylamine, or from technical fatty amines, for example coconut amine, tallow gamine or oleylamine (on this subject, cf. Ullmanns Encyklopädie der technischen Chemie, p. 448, Verlag Chemie, 1976), or from the cyclic amines pyrrolidine, 2,5-dimethylpyrrolidine, piperidine, 2-methylpiperidine, morpholine, 2,6-dimethylmorpholine, hexahydro-1H-azepine, hexahydro-1-(2H)-azocine or octahydro-1H-azonine.

The preferred amino radicals $R^1R^2N$ in the formulae (I) and (II) may be derived formally from the fatty amines coconut amine, tallow gamine or oleylamine, or mixtures thereof, or from dicyclohexylamine or dibenzylamine, most preferably from dibenzylamine.

The serial number n in the formula (I) is an integer, preferably from 4 to 8. Very particular preference is given to the serial number n=6.

In the compounds of the formula (II), $Me^1$ is defined as alkaline earth metal ions when z=2 and is defined as alkali metal or ammonium ions, preferably alkali metal ions, when z=1. From the group of the alkaline earth metal ions, preference is given to calcium and barium ions, very particular preference to barium ions. From the group of the alkali metal ions, preference is given to sodium and potassium ions, very particular preference to sodium ions.

The compounds of the formula (II) are used for the process according to the invention typically in an amount of approx. 180 to 250 mol %, preferably of 190 to 240 mol %, most preferably of 200 to 230 mol %, based on the moles of compounds of the formula (III) used.

The preparation of the compounds of the formula (II) from ammonia or amines and carbon disulphide is known in principle (cf., for example, Houben-Weyl, Methoden der organischen Chemie [Methods of Organic Chemistry], Vol. 9, page 823ff, Georg Thieme Verlag, Stuttgart (1955); Ullmanns Encyklopädie der technischen Chemie, 4th newly revised and extended edition, Vol. 21, p. 89ff, Verlag Chemie, Weinheim (1982); DE-A 22 56 511, page 38).

The preparation of the compounds of the formula (E) is known in principle, for example, from the patent publications EP-A 70 143, DE-A 22 56 511, EP-A 385 972 and EP-A 432 417.

For the preparation process according to the invention, the compounds of the formula (II) and (III) (for example Duralink® HTS from Flexsys, Belgium) may be used in the form of isolated salts or else in the form of their reaction solutions. If necessary, the compounds of the formulae (II) and (III) prepared according to the prior art should be purified in a suitable manner before use for the process according to the invention.

In a novel preparation process (cf. German Patent Application having the application number 102004018193), the compounds of the formula (III) may advantageously be used for the process according to the invention directly in the form of their reaction solutions without further purification. In this novel preparation process for the compounds of the formula (III), the parent $\alpha,\omega$-dihaloalkanes are reacted with thiosulphate ions at a reaction temperature of approximately 80° C. to 150° C. in water without addition of alcohols and/or glycols in a pH range of 3 to 9.8.

The serial number n in the formula (III) has the same definition as in the formula (I). $Me^2$ and $Me^3$ are the same or different in the formula (III) and are each monovalent metal ions or ammonium ions. $Me^2$ and $Me^3$ are preferably the same and are each alkali metal or ammonium ions, preferably alkali metal ions. Of the alkali metal ions, preference is given to sodium and potassium ions, very particular preference to sodium ions.

Useful carbonyl compounds for the process according to the invention may be aldehydes and/or ketones which are fully or only partly water-soluble. Useful examples from the group of the aldehydes are formaldehyde, acetaldehyde or propionaldehyde, preferably formaldehyde. It is of course also possible to use any mixtures of the aldehydes. Useful examples from the group of the ketones are acetone, diethyl ketone, methyl ethyl ketone or methyl propyl ketone, preferably methyl ethyl ketone. It is of course also possible to use any mixtures of the ketones.

It is likewise possible to use any mixtures of the inventive aldehydes and ketones with one another.

When the vapour pressure of the inventive aldehydes and/or ketones is high at the inventive reaction temperature, it is advantageous to work in an autoclave, so that the reaction mixture does not become deficient in these carbonyl compounds as a result of evaporation.

The inventive carbonyl compounds are used as such, i.e. in gaseous or liquid form or as a commercial, aqueous solution (cf. Ullmanns Encyclopädie der technischen Chemie, 4th newly revised and extended edition, Vol. 11, p. 696, Verlag Chemie, Weinheim (1976)).

Of the inventive carbonyl compounds, very particular preference is given to formaldehyde for the preparation process according to the invention, especially in the form of its aqueous solution.

Useful organic solvents for the process according to the invention are from the group of the aromatic solvents benzene, toluene, xylene, ethyl- or diethylbenzene, tetralin, chloro- or dichlorobenzene or anisole. It is of course also possible to use any mixtures of the aromatic solvents.

Useful examples from the group of the aliphatic solvents are straight-chain or branched aliphatic hydrocarbons having 5 to 12 carbon atoms, for example pentane, hexane, heptane or octane, or mixtures thereof. However, it is also possible to use hydrocarbon mixtures which consist predominantly of aliphatic hydrocarbons, for example petroleum ether having a boiling range of approx. 40° to 70° C., light petroleum having a boiling range of approx. 700 to 90° C. or medium petroleum having a boiling range of approx. 90° to 180° C.

Useful examples from the group of the cycloaliphatic solvents are cycloaliphatic hydrocarbons having 5 to 10 carbon atoms such as cyclopentane, methylcyclopentane, cyclohexane, methylcyclohexane, cycloheptane or decaline. It is of course also possible to use any mixtures of the cycloaliphatic hydrocarbons.

Useful examples from the group of the ethers are diethyl ether, di-i-propyl ether, di-n-butyl ether or di-sec-butyl ether, methyl tert-butyl ether or mixtures thereof.

According to the invention, the compounds of the formula (III) which are dissolved fully or partly in water and the salts of the formula (II) which are likewise dissolved fully or partly in water may be reacted with one another in a continuous process, i.e. the two reactants and the inventive ingredients are introduced continually into a reaction tube or into a one-tank or multi-tank battery, and reacted. Preference is given to initially charging the compounds of the formula (III) which are dissolved fully or partly in water in a reaction vessel together with the inventive ingredients and to adding the compounds of the formula (II), continuously or in portions, in solid form or dissolved fully or partly in water. The rate of addition of the compounds of the formula (II) to the initially charged compounds of the formula (III) depends on the reaction temperature selected, on the batch size selected and on the cooling capacity of the reaction vessel available, and can be determined readily by preliminary experiments. When a large amount of heat of reaction can be removed by cooling, a higher metering rate can be selected than when only a small amount of heat of reaction can be removed. Typical metering times for the compounds of the formula (II) dissolved, for example, fully in water into the initial charge comprising aqueous and organic solvents and the fully or partly dissolved compounds of the formula (III) are, for example, 0.25 to 5 h, preferably 0.5 to 3 h. For still longer metering times, there is technically no limitation, but they might generally not be economically viable. It is of course also possible to proceed in the reverse manner, i.e. the compounds of the formula (III) may be added continuously or in portions, in solid form or dissolved fully or partly in water, to the compounds of the formula (II) which are dissolved fully or partly in water and have been initially charged together with the inventive ingredients.

Preference is given to adding the reactant which is added to the initially charged reactant in fully dissolved form.

The inventive carbonyl compounds are used in amounts of approx. 5 to 600 mol % based on the moles of compounds of the formula (III) used. The most favourable amount of carbonyl compounds can be determined readily by preliminary experiments. In the preferred preparation process in which the compounds of the formula (II) are added to the compounds of the formula (III) in the initial charge, approx. 5 to 300 mol %, preferably 10 to 200 mol %, of carbonyl compounds, based on the moles of compounds of the formula (III) used, are used at long reaction times, i.e. at postreaction times of more than 10 h, calculated from the end of the addition of the aqueous solutions of the compounds of the formula (II). At shorter reaction times, i.e. at postreaction times of about 0.5 to about 10 h, calculated from the end of the addition of the aqueous solutions of the compounds of the formula (II), 25 to 600 mol %, preferably 37 to 550 mol %, most preferably 50 to 500 mol %, of carbonyl compounds are used, based on the moles of compounds of the formula (III) used.

The solubility of the compounds of the formula (III) in water depends upon the type of the cations $Me^2$ and $Me^3$, on the serial number n and on the temperature of the water solvent. The solubility of these compounds at the selected water temperature can be found out readily by experiments. With rising temperature, the solubility of the compounds of the formula (III) in water generally increases. In the case of the disodium salt dihydrate of hexamethylene 1,6-bisthiosulphate, it is still possible to prepare approx. 51% aqueous solutions at approx. 70° C.

The solubility of the compounds of the formula (II) in water depends on the $R^1$ and $R^2$ radicals, on the type of the cation $Me^1$ and on the temperature of the water solvent. The solubility of these compounds at the selected water temperature can be found out readily by experiments. With rising temperature, the solubility of the compounds of the formula (II) in water generally increases. In the case of sodium dibenzyldithiocarbamate, it is readily possible to prepare approx. 17 to 21% aqueous solutions at approx. 20° C.

The use of aqueous solutions of the compounds of the formula (II) and (III) in very low concentration does not have any technical limitations, but is just uneconomic for the process according to the invention and not advantageous from the point of view of minimum amounts of wastewater.

The process according to the invention is carried out at a reaction temperature of approx. 0° to 90° C., preferably of 5° to 85° C., most preferably of 10° to 80° C., and in a pH range of approx. 7 to 14, preferably of 8 to 14, most preferably of 8.5 to 13.5, up to a yield of at least 80% of theory, preferably of at least 85% of theory, based on the compounds of the formula (III) used.

The pH values in the inventive pH range are established and controlled, depending on the current pH situation, preferably with acids, preferentially with inorganic acids, for example hydrochloric acid or sulphuric acid, or mixtures thereof, or with bases, preferably with inorganic bases, for example sodium hydroxide solution or potassium hydroxide solution, or mixtures thereof. Depending on the pH of the compounds of the formula (II) and (III) dissolved in water, it is not necessary under some circumstances to specially establish the inventive pH range, since this is established by itself (cf. Example 2). It is of course possible in the context of the present invention to commence with the reaction of the compounds of the formula (III) which, in the preferred preparation process, are disposed in the initial charge with the compounds of the formula (II) which are disposed in the feed even at a pH lower than 7, in which case the important factor is that, when the alkali compounds of the formula (II) are added to the initial charge comprising the compounds of the formula (III), the pH of the aqueous reaction mixture rises very rapidly into the preferred pH range of 8 to 14; otherwise these pH ranges have to be established appropriately by addition of inorganic acids or bases. The lower limit of the preferred pH range of 8 after addition of at most 20 parts by weight, preferably of at most 10 parts by weight, based on 100 parts by weight of the amount of compounds of the formula (II) to be used in accordance with the invention, should preferably be attained. After the addition of the compounds of the formula (II) to the compounds of the formula (III), the reaction is preferably conducted to completion in the optimal pH range of approx. 9 to 13.

In a preferred embodiment of the invention, the optimal pH range of approx. 9 to 13 is advantageously established with potassium hydrogencarbonate or sodium hydrogencarbonate, preferably with sodium hydrogencarbonate. The amount of potassium hydrogencarbonate or sodium hydrogencarbonate to be used is approx. 1 to 300 parts by weight, preferably 25 to 200 parts by weight, most preferably 50 to 150 parts by weight, based on 100 parts by weight of the theoretically expected amount of compounds of the formula (I). The inventive amount of alkali metal hydrogencarbonate may be initially charged all at once immediately before the start of the reaction together with the aqueous solutions/dispersions of compounds of the formula (III) in solid form or else be initially charged as an aqueous solution or be added during the reaction to the reaction mixture in portions or else continuously, in solid form or else as an aqueous solution. Preference is given to adding the inventive amount of alkali metal hydrogencarbonate all at once to establish the optimal pH range in the initial charge comprising the inventive ingredients and compounds of the formula (III) immediately before the aqueous solutions of the compounds of the formula (II) are fed in. This typically establishes a pH in the range of approx. 7 to 9. During the feeding of the compounds of the formula (II), the pH of the reaction mixture rises rapidly and, on completion of the feeding including the subsequent continued stirring time, is then within the optimal pH range of approx. 9 to 13.

For the preparation process according to the invention, the organic solvents are used in amounts of approx. 2 to 100 000 parts by weight, preferably of 3 to 10 000 parts by weight, most preferably of 4 to 2000 parts by weight, based on 100 parts by weight of the theoretically expected amounts of compounds of the formula (I). With regard to these amounts of solvent, there are two process variants. In the first process variant, only a little solvent is used, i.e. the amount of solvent is so small that only a minor amount of the amount of compounds of the formula (I) which forms overall is dissolved in the selected solvent under reaction conditions. This is known as the slurry process, i.e. especially at the end of the reaction, a solid phase is present in addition to liquid phases. In the second process variant, a lot of solvent is used, i.e. the amount of solvent is sufficiently large that the entire amount of compounds of the formula (I) formed is dissolved in the selected solvent under the reaction conditions. This is known as the solution process, i.e. only liquid phases are present during and at the end of the reaction. The two variants are illustrated in detail below.

In the slurry process, the inventive organic solvents are used in amounts of approx. 2 to 100 parts by weight, preferably of 3 to 95 parts by weight, most preferably of 4 to 90 parts by weight, based on 100 parts by weight of the theoretically expected amount of compounds of the formula (I).

The most favourable amount of solvent for the slurry process can be determined readily by preliminary experiments. It is to be selected depending on the type of solvent and the reaction temperature such that only small amounts of the compounds of the formula (I) are dissolved in the organic solvent at the end of the reaction. The majority of the compounds of the formula (I) should be present undissolved after their formation, i.e. as a solid in the liquid phases. In the context of the invention, the amount of the compounds of the formula (I) dissolved in the organic solvent at the end of the reaction in the slurry process should be at most 15 parts by weight, preferably at most 10 parts by weight, based on 100 parts by weight of product isolable by solid-liquid separation (for example by filtration, suction filtration or centrifugation).

In the slurry process, it is favourable when a small amount of the compounds of the formula (I) dissolves in the selected solvent under reaction conditions. According to our estimations, this amount is at least 0.01 part by weight, preferably at least 0.1 part by weight, based on 100 parts by weight of product isolable by solid-liquid separation.

For the slurry process, preferred solvents are toluene, hexane, light petroleum having a boiling range of approx. 70 to 90° C., cyclohexane or methyl tert-butyl ether. However, mixtures of these solvents with one another are also useful as the process solvent. Very particular preference is given to toluene as the solvent.

In the slurry process, the inventive reaction temperature is within a selected temperature range of approx. 0° to 60° C., preferably of 5° to 55° C., most preferably of 10° to 50° C.

In the slurry process, the precipitated compounds of the formula (I) are removed preferably by solid-liquid separation, for example by filtration (e.g. filter press), by centrifugation or by suction filtration. After the solid compounds of the formula (I) have been removed from the mother liquor, they are washed with deionized water and dried in a suitable manner.

To use the compounds of the formula (1) as a vulcanizing agent for diene rubber, they are typically ground and optionally admixed for the purpose of dust suppression with a suitable oil, for example mineral oil, which does not have any adverse influence on the performance properties of the compounds of the formula (I).

In the solution process, in contrast, the inventive organic solvents are used in amounts of approx. 105 to 100 000 parts by weight, preferably of 120 to 10 000 parts by weight, most preferably of 150 to 2000 parts by weight, based on 100 parts by weight of the theoretically expected amount of compounds of the formula (I).

The minimum required amount of solvent for the solution process according to the invention can be determined readily by preliminary experiments. It is to be selected depending on the type of solvent and the reaction temperature in such a way that the amounts of compounds of the formula (I) formed are dissolved fully in the organic solvent at the end of the reaction.

For the solution process, preferred solvents are toluene, xylene or chlorobenzene. However, it is also possible to use mixtures of these solvents with one another as the process solvent. Very particular preference is given to toluene or chlorobenzene as the solvent.

In the solution process, the inventive reaction temperature is within the temperature range of approx. 0° to 90° C., preferably of 5° to 85° C., most preferably of 10° to 80° C.

In the solution process, the organic phase is removed from the aqueous phase on completion of reaction. If desired, the separated organic phase may be washed with water. To obtain the compounds of the formula (I), the organic process solvent may be evaporated, preferably under reduced pressure, and then the resulting viscous oil brought to crystallization, which is generally very difficult and time-consuming. As in the slurry process, the compounds of the formula (I) can then be ground and admixed for the purpose of dust suppression with a suitable oil. In order to circumvent the complicated process steps of grinding and oiling, the organic solutions consisting of process solvent and the compounds of the formula (I) dissolved therein may advantageously be contacted with a support and then the organic solvent evaporated. The contacting may be effected, for example, in such a way that the support is initially charged in a suitable mixer vessel (for example Lödige mixer) and then the organic solvent is sprayed in finely divided form onto the support, in the course of which the solvent simultaneously evaporates, resulting in the support becoming coated with the compounds of the formula (I). Preference is given to evaporating the solvent under reduced pressure, in the course of which the temperature of the support is in the range of approx. 20° to 80° C., preferably in the range of 30° to 70° C.

Useful supports for the contacting with the inventive organic solutions which comprise the compounds of the formula (I) are, for example, silicates, clay earth, kaolin, siliceous earth, talc, chalk, metal oxides, metal carbonates, kieselguhr, carbon blacks and/or silica. Preference is given to using kieselguhr, carbon black and/or silica. Of the carbon blacks, preference is given to those which have a DBP number of >30 ml/100 g, preferably >50 ml/100 g. The carbon blacks may be used in the form of powder or in bead form. Preference is given to using the carbon blacks in bead form. Of the silicas, preference is given to using high-dispersity grades. High-dispersity silicas are prepared, for example, by precipitating solutions of silicates or by flame hydrolysis of silicon halides, and have a specific surface area of 20 to 400 m$^3$/g (BET surface area), preferably of 100 to 250 m$^3$/g, most preferably of 120 to 200 m$^3$/g, and a primary particle size of 10 to 400 nm. The silicas may be used in the form of powder, in the form of granule or in the form of microgranule. Preference is given to using microgranule.

The mass ratio of the supports to be used to the compounds of the formula (I) to be applied to the supports is approx. 7:3 to 3:7, preferably 6:4 to 4:6.

The solution process according to the invention, coupled with the coating, described here, of supports with the compounds of the formula (I), does not require the complicated grinding and optionally oiling of the compounds of the formula (I) for use, for example, as a vulcanizing agent for diene rubbers. Taking into account the active substance content on the support, the supports coated with the compounds of the formula (I) may themselves be used for the vulcanization, like the compounds of the formula (I) themselves.

EXAMPLES

In the examples which follow, the pH was in each case determined with a pH electrode.

Example 1

A nitrogen-purged stirred 2 l four-necked flask apparatus with internal thermometer, reflux condenser with bubble counter and pH electrode was initially charged with 99.6 g (0.25 mol) of the disodium salt dihydrate of hexamethylene 1,6-bisthiosulphate (Duralink® HTS, 98% product from Flexsys, Belgium) dissolved in 300 g of deionized water. The stirrer was switched on. 21.0 g (0.25 mol) of sodium hydrogencarbonate, 21.0 g (0.25 mol) of aqueous formaldehyde solution (36-38%) and 43.3 g of toluene (25 parts by weight based on 100 parts by weight of the theoretically expected yield of 1,6-bis(N,N-dibenzylthiocarbamoyldithio)hexane) were added. The headspace of the reaction vessel was purged once again briefly with nitrogen. At an internal reactor temperature of 23° C., after the sodium hydrogencarbonate had been dissolved, the feed of the sodium dibenzyldithiocarbamate solution (NaBEC solution) which had a temperature of approx. 22° C. was then commenced. In total, 864 g (0.5 mol) of aqueous NaBEC solution (17.1%) were added dropwise uniformly over 0.5 h, in the course of which the reaction temperature was still kept at approx. 23° C. by cooling. The mixture was then stirred at this temperature for a further 22 h. Immediately before the commencement of the NaBEC feeding, the pH was approx. 8.4. In the course of the feeding of the NaBEC solution, the pH rose very sharply and attained a value of approx. 11.1 at the end of the NaBEC feeding. At the end of the continued stirring time, the pH was still approx. 11.1. It was possible to isolate the precipitated solid very readily by suction filtration. The solid on the suction filter was washed with a total of 3 l of deionized water in portions, which proceeded very easily. The product was dried at approx. 50° C. and approx. 150 mbar in a vacuum drying cabinet to constant weight. The yield of 1,6-bis(N,N-dibenzylthiocarbamoyldithio)hexane was approx. 96% based on the disodium salt dihydrate of hexamethylene 1,6-bisthiosulphate used. The melting point of the resulting product was approx. 93° C. and the content (HPLC, external standard) was approx. 99%. The ignition residue (750° C./2 h) was determined to be approx. 0.02% by weight.

Example 2

The procedure of Example 1 was repeated, except that no sodium hydrogencarbonate was used and the NaBEC solution (19.1%; 773.3 g) which had a temperature of approx. 22° C. was added dropwise uniformly within 1 h. Immediately before the commencement of the NaBEC feeding, the pH was approx. 8.6. In the course of the feeding of the NaBEC solution, the pH rose very sharply and attained a value of approx. 12.5 at the end of the NaBEC feeding. At the end of the continued stirring time, the pH was approx. 12.4. It was possible to isolate the reaction product formed very readily by suction filtration and subsequently to wash it without any problem. The yield of 1,6-bis-(N,N-dibenzylthiocarbamoyldithio)hexane was approx. 94% based on the disodium salt dihydrate of hexamethylene 1,6-bisthiosulphate used. The content (HPLC, external standard) was approx. 98%, the melting point approx. 92° C. The ignition residue (750° C./2 h) was determined to be approx. 0.05% by weight.

Example 3

The procedure was analogous to Example 1. All of the feedstocks to be initially charged were initially charged in the flask apart from sodium hydrogencarbonate. The pH of this initial charge was adjusted to approx. 13 with 45% sodium hydroxide solution at approx. 20° C. (use of 45% sodium hydroxide solution approx. 13.1 g). The NaBEC solution (19.1%; 773.3 g) which had a temperature of approx. 22° C. was then added dropwise uniformly within 1 h. During the NaBEC feeding and during the subsequent postreaction of 22 h, the pH of the reaction mixture was kept at pH 13 by addition of 5% sodium hydroxide solution by means of a pH-controlled metering pump. It was possible to isolate the reaction product which formed readily by suction filtration and subsequently to wash it without any problem. The yield of 1,6-bis(N,N-dibenzylthiocarbamoyldithio)hexane was approx. 94% based on the disodium dihydrate salt of hexamethylene 1,6-bisthiosulphate used. The content (HPLC, external standard) was approx. 97%, the melting point approx. 92° C.

Example 4

A nitrogen-purged stirred 2 l four-necked flask apparatus with internal thermometer, reflux condenser with bubble counter and pH electrode was initially charged with 136.5 g (0.55 mol) of sodium thiosulphate pentahydrate and 300 g of deionized water. The stirrer was switched on. After the thiosulphate had dissolved, 38.8 g (0.25 mol) of 1,6-dichlorohexane were added. The weakly acidic mixture was adjusted to pH 7.2±0.1 with 2.5% sodium hydroxide solution. The reaction vessel was purged once again briefly with nitrogen and the mixture was then boiled at reflux for 9 h, and the pH of the reaction mixture was kept at 7.2±0.1 during this time by addition of 2.5% sodium hydroxide solution by means of a metering pump (control by means of pH electrode). After in each case 6 and 8 hours of the reaction, the bubble counter was removed briefly from the reflux condenser. In each case approx. 5 ml of demineralized water were then sprayed with a wash bottle into the reflux condenser from the top in order to flush back into the flask any 1,6-dichlorohexane which has not dripped back. After the reaction time had ended, approx. 15 ml of 2.5% sodium hydroxide solution were used for pH control. After brief cooling, a small sample was taken from the reaction mixture to determine the conversion of 1,6-dichlorohexane by gas chromatography (GC). The GC analysis with internal standard gave a residual content of 1,6-dichlorohexane <10 ppm, which corresponds to a conversion of 1,6-dichlorohexane of >99.9%. The reaction mixture cooled to room temperature was admixed with 21.0 g (0.25 mol) of aqueous formaldehyde solution (36-38%), 21.0 g (0.25 mol) of sodium hydrogencarbonate and 43.3 g of toluene (25 parts by weight based on 100 parts by weight of the theoretically expected yield of 1,6-bis(N,N-dibenzylthiocarbamoyldithio)hexane). The headspace of the reactor was purged once again briefly with nitrogen. As soon as the hydrogencarbonate had dissolved, the feed of 773.3 g (0.5 mol) of sodium dibenzyldithiocarbamate solution (NaBEC solution) (19.1%) which had a temperature of approx. 22° C. was commenced at an internal reactor temperature of approx. 23° C. During the uniform feeding of the NaBEC solution over 1 h, the internal reactor temperature was kept at approx. 23° C. On completion of feeding, the mixture was stirred at approx. 23° C. for a further 22 h. Immediately before the commencement of the NaBEC feeding, the pH was approx. 8.3. On commencement of the NaBEC feeding, the pH rose very sharply and attained a value of approx. 10.7 at the end of the NaBEC feeding. At the end of the continued stirring time, the pH was likewise approx. 10.7. It was possible to isolate the precipitated solid very readily by suction filtration. The product was washed on the suction filter with a total of 2 l of demineralized water in portions, which proceeded very easily. The product was dried at 50° C. and approx. 150 mbar in a vacuum drying cabinet to constant weight. The yield was approx. 91% of theory based on 1,6-dichlorohexane used. The content of 1,6-bis(N,N-dibenzylthiocarbamoyldithio) hexane was determined to be approx. 96% by means of HPLC (external standard). The melting point was approx. 92° C. The ignition residue (750° C./2 h) of the product was approx. 0.2% by weight.

Examples 5 to 7

The procedure was analogous to Example 1. However, the amounts of toluene, the reaction temperature and the feeding time were varied. The continued stirring time on completion of feeding was in each case 5 h. The temperature of the feed of sodium dibenzyldithiocarbamate solution (NaBEC solution) was in each case approx. 22° C. It was possible very readily to remove the resulting reaction products by suction filtration. The subsequent washing was carried out with deionized water in portions, which proceeded very easily.

TABLE 1

|  | Example 5 | Example 6 | Example 7 |
| --- | --- | --- | --- |
| Reaction temperature (° C.) | 23 | 23 | 40 |
| NaBEC solution |  |  |  |
| Feeding time (h) | 0.5 | 1 | 0.5 |
| Amount used (g) | 815 | 901 | 815 |
| Concentration (%) | 18.1 | 16.4 | 18.1 |
| Amount of toluene (g) | 26.0 | 87.0 | 17.3 |
| (parts by weight)[1] | 15.0 | 50.2 | 10.0 |
| Yield of 1,6-bis- | 97 | 92 | 95 |
| (N,N-dibenzylthio- |  |  |  |
| carbamoyldithio)- |  |  |  |
| hexane based on |  |  |  |
| Duralink ® HTS (%) |  |  |  |
| Content, HPLC[2](%) | 97 | 99 | 99 |

[1]based on 100 parts by weight of theoretically expected yield of 1,6-bis(N, N-dibenzylthiocarbamoyldithio)hexane.
[2]external standard Examples 8 to 10

The procedure was analogous to Example 1, except with different solvents under different reaction temperatures. The feed of the sodium dibenzyldithiocarbamate solution (NaBEC solution) in each case had a temperature of approx. 22° C. It was possible very readily to isolate and wash the reaction products.

TABLE 2

|  | Example 8 | Example 9 | Example 10 |
| --- | --- | --- | --- |
| Reaction temperature (° C.) | 40 | 23 | 23 |
| Solvent | n-hexane | chlorobenzene | cyclohexane |
| Amount of solvent (g) | 33 | 11.1 | 54.5 |
| (parts by weight)[1] | 19.0 | 6.4 | 31.5 |
| NaBEC solution |  |  |  |
| Feeding time (h) | 0.5 | 1 | 1 |
| Amount used (g) | 815 | 1019 | 1019 |
| Concentration (%) | 18.1 | 14.5 | 14.5 |

TABLE 2-continued

|  | Example 8 | Example 9 | Example 10 |
| --- | --- | --- | --- |
| Yield of 1,6-bis- | 94 | 95 | 95 |
| (N,N-dibenzylthio- |  |  |  |
| carbamoyldithio)- |  |  |  |
| hexane based on |  |  |  |
| Duralink ® HTS (%) |  |  |  |
| Content, HPLC[2] (%) | 99 | 99 | 99 |
| Melting point (° C.) | 94 | 93 | 93 |

[1]based on 100 parts by weight of the theoretically expected yield of 1,6-bis (N,N-dibenzylthiocarbamoyldithio)hexane compound
[2]external standard In Example 9, the reaction product was initially washed with methanol on the suction filter in order to displace the chlorobenzene more rapidly. Only then was it washed with deionized water. In Examples 8 and 10, the reaction products were washed on the suction filter only with deionized water.

Examples 11 and 12

The procedure corresponded to Example 1, except the amount of formaldehyde used was varied and the continued stirring time after addition of the NaBEC solution was in each case shortened to 1 h. The feed of the sodium dibenzyldithiocarbamate solution (NaBEC solution) in each case had a temperature of approx. 22° C. The reaction products were washed on the suction filter with deionized water in portions, which proceeded very readily.

TABLE 3

|  |  | Example 11 | Example 12 |
| --- | --- | --- | --- |
| Amount of formaldehyde solution (37-38%) | (g) | 21 | 84 |
| Formaldehyde based on Duralink ® HTS | (mol %) | 105 | 420 |
| NaBEC solution |  |  |  |
| Feeding time | (h) | 1 | 1 |
| Amount used | (g) | 890 | 890 |
| Concentration | (%) | 16.6 | 16.6 |
| Yield of 1,6-bis- | (%) | 87 | 93 |
| (N,N-dibenzylthio- |  |  |  |
| carbamoyldithio)- |  |  |  |
| hexane based on |  |  |  |
| Duralink ® HTS |  |  |  |
| Content, HPLC[1] | (%) | 99 | 99 |
| Melting point | (° C.) | 93 | 93 |

[1]external standard

Example 13

A nitrogen-purged stirred 4 l four-necked flask apparatus with internal thermometer, reflux condenser and pH electrode was initially charged with 240 g of deionized water, 79.7 g (0.20 mol) of the disodium salt dihydrate of hexamethylene 1,6-bisthiosulphate (Duralink® HTS, 98%, from Flexsys, Belgium), 16.8 g (0.20 mol) of sodium hydrogencarbonate, 16.8 g (0.20 mol) of aqueous formaldehyde solution (35.8%) and 779 g of toluene (562 parts by weight based on 100 parts by weight of the theoretically expected yield of 1,6-bis(N,N-dibenzylthiocarbamoyldithio)hexane. The reaction vessel was purged once again briefly with nitrogen and then heated to 50° C. At an internal reactor temperature of 50° C., the feed of sodium dibenzyldithiocarbamate (NaBEC) solution which had a temperature of approx. 22° C. was commenced. In total, 721 g (0.4 mol) of aqueous NaBEC solution (16.4%) were added dropwise uniformly over 1 h, in the course of which the reaction temperature was still kept at 50° C. The mixture was then stirred at this temperature for a further 5 h. Immediately before the commencement of the NaBEC feed, the pH was approx. 8.5. On commencement of the NaBEC feeding, the pH rose sharply and attained a value of approx. 10.8 at the end of the NaBEC feeding. At the end of the continued stirring time, the pH at 50° C. was still approx. 10.8 and all reaction product formed had dissolved fully in toluene. After the phase separation, the organic phase was washed four times with approx. 50 ml each time of deionized water and then the toluene was concentrated by evaporation on a rotary evaporator under reduced pressure at a bath temperature of approx. 50° C. It was possible to bring the resulting viscous oil to crystallization only with difficulty. The crystals which were eventually obtained were dried in a vacuum drying cabinet at approx. 50° C. and approx. 150 mbar to constant weight. The yield was approx. 95% based on the disodium salt dihydrate-hexamethylene 1,6-bisthiosulphate used. The melting point of the product was determined to be approx. 92° C., the content of 1,6-bis(N,N-dibenzylthiocarbamoyldithio)hexane to be approx. 98% (HPLC, external standard) and the ignition residue (750° C./2 h) to be 0.01% by weight.

Examples 14 and 15

The procedure was as in Example 13, except that the reaction was carried out at a reaction temperature of 23° and 70° C. The feed of the sodium dibenzyldithiocarbamate solution (NaBEC solution) in each case had a temperature of approx. 22° C.

TABLE 4

|  |  | Example 14 | Example 15 |
|---|---|---|---|
| Reaction temperature NaBEC solution | (° C.) | 23 | 70 |
| Amount used | (g) | 720.5 | 695.1 |
| Concentration | (%) | 16.4 | 17.0 |
| Yield of 1,6-bis-(N,N-dibenzylthio-carbamoyldithio)-hexane based on Duralink ® HTS |  (%) | 97 | 89 |
| Content, HPLC[1] | (%) | 99 | 97 |
| Melting point | (° C.) | 93 | 92 |

[1]external standard

N.B.: In both examples, all of the reaction product formed was dissolved in toluene at the end of the reaction at the particular reaction temperature. The viscous oil obtained in each case after workup crystallized only very slowly.

Example 16

50 g of Zeosil® 1165 MP silica (product from Rhodia Silica Systems) were initially charged in a 1 l round-bottomed flask and then admixed in small portions with a total of 337.8 g of an approx. 14.8% solution of 1,6-bis(N,N-dibenzylthiocarbamoyldithio)hexane in toluene, and the solvent was evaporated on a rotary evaporator on a water-jet pump vacuum and a maximum bath temperature of 75° C. after the addition of each portion without the product temperature rising above 50° C. Subsequently, the coated silica was dried to constant weight in a vacuum drying cabinet at approx. 50° C. and approx. 150 mbar. A coated, virtually lump-free, free-flowing, virtually non-dusting microgranule was obtained, whose content of 1,6-bis(N,N-dibenzylthiocarbamoyldithio) hexane was approx. 48% (HPLC, external standard).

Examples 17 and 18

Comparative Examples Analogous to DE-A 22 56 511, Page 39

A nitrogen-purged stirred 2 l four-necked flask apparatus with internal thermometer and reflux condenser was initially charged with 300 g of deionized water and 99.6 g (0.25 mol) of the disodium salt dihydrate of hexamethylene 1,6-bisthiosulphate (Duralink® HTS, 98% product from Flexsys, Belgium). 102.1 g (0.75 mol) of sodium acetate trihydrate and 48.0 g (0.583 mol) of aqueous formaldehyde solution (36.5%) were added. After all of the sodium acetate trihydrate had been dissolved, 971.7 g (0.5 mol) of aqueous sodium dibenzyldithiocarbamate solution (NaBEC solution) (15.2%) which had a temperature of approx. 22° C. were added dropwise uniformly at an internal reactor temperature of approx. 23° C. over 1 h. In Example 17, the pH was 8.7 immediately before commencement of the NaBEC feeding, 12.4 at the end of the feeding. In the case of Example 18, the pH was 9.4 immediately before commencement of feeding and 12.4 at the end of feeding. The mixture was stirred at approx. 22° C. for a further 5 h in Example 17 and for a further 22 h in Example 18. The solids which were in each case white and extremely fine were isolated by filtration and washed thoroughly with in each case a total of 4 l of deionized water in portions. Owing to the high fineness of the crystals, the isolation and the washing of the products was very laborious and difficult. The washed reaction product was dried at approx. 50° C. and approx. 150 mbar in a vacuum drying cabinet.

TABLE 5

|  |  | Example 17 (Comparison) | Example 18 (Comparison) |
|---|---|---|---|
| Continued stirring time | (h) | 5 | 22 |
| Yield of 1,6-bis-(N,N-dibenzylthio-carbamoyldithio)-hexane based on Duralink ® HTS | (%) | 82 | 86 |
| Content, HPLC[1] | (%) | 93 | 97 |
| Melting point | (° C.) | 85 | 89 |
| Ignition residue (750° C./2 h) | (% by wt.) | 0.3 | 0.3 |

[1]external standard

Evaluation: it is found that a lower yield, a lower active substance content and a lower melting point are obtained according to the prior art in comparison to inventive Example 1.

Examples 19 and 20

Comparative Examples Analogous to EP-A 432 417, Page 4, Line 50ff

The procedure was analogous to Example 1, except without application of the inventive measures, i.e. without use of formaldehyde, sodium hydrogencarbonate and toluene. In Example 19, the pH was approx. 8.6 immediately before commencement of feeding of the NaBEC solution, approx. 9.3 at the end of feeding and approx. 9.7 at the end of the continued stirring time of 5 h. In Example 20, the pH was approx. 8.7 immediately before commencement of feeding of the NaBEC solution, approx. 9.5 at the end of feeding and approx. 9.9 at the end of the continued stirring time of 22 h. Owing to the fine crystals, the reaction product obtained in Examples 19 and 20 was very difficult to wash and took a very long time.

TABLE 6

|  |  | Example 19 (Comparison) | Example 20 (Comparison) |
|---|---|---|---|
| NaBEC solution |  |  |  |
| Feeding time | (h) | 0.5 | 0.5 |
| Amount used | (g) | 777.3 | 777.3 |
| Concentration | (%) | 19.1 | 19.1 |
| Continued stirring time | (h) | 5 | 22 |
| Yield of 1,6-bis-(N,N-dibenzylthio-carbamoyldithio)-hexane based on Duralink ® HTS | %) | 74 | 78 |
| Content, HPLC[1)] | (%) | 96 | 91 |
| Melting point | (° C.) | 81–84 | 80–90 |
| Ignition residue (750° C./2 h) | (% by wt.) | 0.15 | 0.98 |

[1)]external standard

Evaluation.: According to the prior art, very fine products whose washing is very difficult and only very slow are obtained in low yield. The low yield, the low active substance content and the wide melting range of the product in Example 20 become particularly clear in direct comparison with inventive Examples 1 and 2.

The present invention has been described with reference to specific details of particular embodiments thereof. It is not intended that such details be regarded as limitations upon the scope of the invention except insofar as and to the extent that they are included in the accompanying claims.

As set forth herein it shall be understood that theoretical yield shall mean the amount of product predicted by a balanced equation when all of the limiting reagent has reacted. Actual yield shall mean the amount of product actually obtained per the practice of the reaction. Percent yield shall mean the proportion of the actual yield to the theoretical yield as defined by the following formula, Percent Yield=(actual yield/theoretical yield)×100.

It should also be understood, as used throughout this specification a reference to a yield given as a percentage refers to the percent yield; furthermore, reference to a theoretically expected amount shall be understood to refer to the theoretical yield.

It must be noted that, as used in this specification and the appended claims, the singular forms "a," "an," and "the" include plural referents unless the content clearly dictates otherwise.

What is claimed is:

1. Process for preparing a compound of the formula (I)

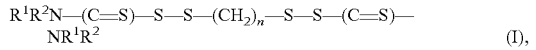

wherein the $R^1$ and $R^2$ radicals are each independently selected from the group consisting of hydrogen, alkyl, cycloalkyl, aralkyl, phenyl, substituted phenyl, alkylaryl, and a heterocyclic ring having 4 to 8 carbon atoms including at least one nitrogen atom, and where n is an integer from 2 to 8, comprising the step of reacting a compound of the formula (II)

wherein $R^1$ and $R^2$ radicals are each as defined in the formula (I) and z=1 when $Me^1$ is an alkali metal or ammonium ion and z=2 when $Me^1$ is an alkaline earth metal ion, with the a compound of the formula (III)

wherein $Me^2$ and $Me^3$ are the same or different and are each monovalent metal ions or ammonium ions and n is as defined in the formula (I), wherein said step of reacting is performed in the presence of water, a carbonyl containing compound and an organic solvent, in a pH range of 7 to 14 at a reaction temperature of 0° to 90° C., until the compound of the formula (I) reaches a percent yield of at least 80% based on the salts of the formula (III), further wherein the amount of the compound of the formula (II) is 180 to 250 mol % based on the moles of the compound of the formula (III) used, the amount of the carbonyl containing compound is 5 to 600 mol % based on the moles of the compound of the formula (III) used, and the amount of the organic solvent is 2 to 100,000 parts by weight based on 100 parts by weight of the theoretical yield of the compound of the formula (I).

2. The process according to claim 1, wherein the organic solvent is used in an amount of 2 to 100 parts by weight based on 100 parts by weight of the theoretically yield expected of the compound of the formula (I) and the reaction temperature is in the range of 0 to 60° C., further wherein a portion of the compound of the formula (I) is found at the end of the reaction to be dissolved in the organic solvent and where the amount of the compound of the formula (I) dissolved in the organic solvent at the end of the reaction is at most 15 parts by weight based on 100 parts by weight of the compound of the formula (I).

3. The process according to claim 1, wherein the organic solvent is used in an amount of 105 to 100,000 parts by weight based on 100 parts by weight of the theoretical yield expected of the compound of the formula (I) and the reaction temperature is in the range of 0° to 90° C., and wherein the compound of the formula (I) are found to be dissolved fully in the organic solvent at the end of the reaction, thereby forming a reaction solution.

4. The process according to claim 3, further comprising: contacting the reaction solution, comprising the organic solvent, with a support and subsequently evaporating the organic solvent.

5. The process according to claim 4, wherein said support is at least one of silicate, clay earth, kaolin, siliceous earth, talc, chalk, metal oxide, metal carbonate, carbon black or silica.

* * * * *